(12) United States Patent
Wiederin et al.

(10) Patent No.: US 8,847,102 B2
(45) Date of Patent: Sep. 30, 2014

(54) TORCH ASSEMBLY

(75) Inventors: Daniel R. Wiederin, Omaha, NE (US); Gary J. Barret, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 595 days.

(21) Appl. No.: 13/084,208

(22) Filed: Apr. 11, 2011

(65) Prior Publication Data

US 2011/0248003 A1  Oct. 13, 2011

Related U.S. Application Data

(60) Provisional application No. 61/322,740, filed on Apr. 9, 2010.

(51) Int. Cl.
*B23K 10/00* (2006.01)
*H05H 1/30* (2006.01)

(52) U.S. Cl.
CPC ........................................ *H05H 1/30* (2013.01)
USPC ............ 219/121.49; 219/121.52; 219/121.51; 315/111.51

(58) Field of Classification Search
CPC ............. B23K 10/00; H05H 1/30; H05H 1/34
USPC .......................... 219/121.52, 121.51, 121.48; 315/111.51, 111.21
See application file for complete search history.

(56) References Cited

U.S. PATENT DOCUMENTS

| | | | | |
|---|---|---|---|---|
| 4,035,604 A | * | 7/1977 | Meleka et al. | 219/121.44 |
| 4,266,113 A | * | 5/1981 | Denton et al. | 219/121.51 |
| 4,482,246 A | * | 11/1984 | Meyer et al. | 356/316 |
| 5,051,557 A | * | 9/1991 | Satzger | 219/121.52 |
| 5,288,969 A | | 2/1994 | Wong et al. | |
| 5,908,566 A | * | 6/1999 | Seltzer | 219/121.52 |
| 7,847,210 B2 | | 12/2010 | Brezni et al. | |
| 7,967,891 B2 | * | 6/2011 | Paserin et al. | 75/346 |
| 8,232,500 B2 | * | 7/2012 | Brezni et al. | 219/121.48 |
| 8,289,512 B2 | * | 10/2012 | Morrisroe | 356/316 |
| 2009/0059221 A1 | | 3/2009 | Hammer | |

* cited by examiner

*Primary Examiner* — Mark Paschall
(74) *Attorney, Agent, or Firm* — Advent, LLP

(57) ABSTRACT

A demountable plasma torch assembly suitable for use in ICP spectrometry comprises a first tube having an inner diameter and a second tube disposed concentrically within the first tube, wherein the second tube has an outer diameter that is less than the inner diameter of the first tube. The first and second tubes are supported by a torch body. The torch body includes a first bore configured to receive an end of the first tube, a second bore configured to receive an end of the second tube, and a manifold disposed between the first bore and the second bore to receive a gas for injection between the first tube and the second tube. The manifold has an outer diameter at least substantially equal to the inner diameter of the first tube and an inner diameter at least substantially equal to the outer diameter of the second tube.

18 Claims, 5 Drawing Sheets

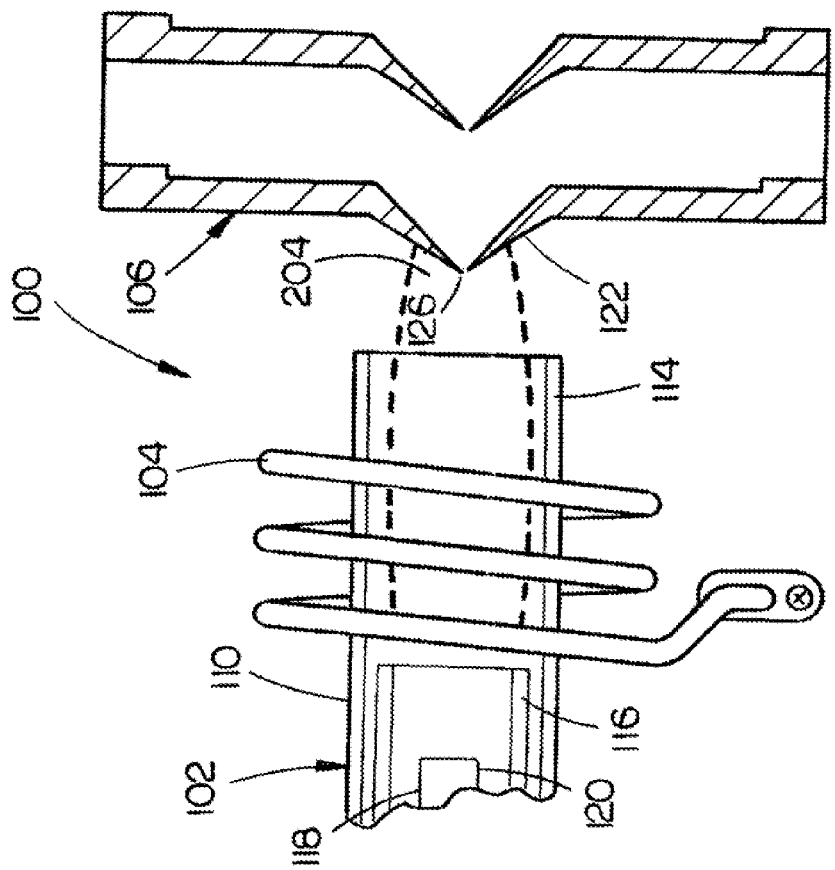
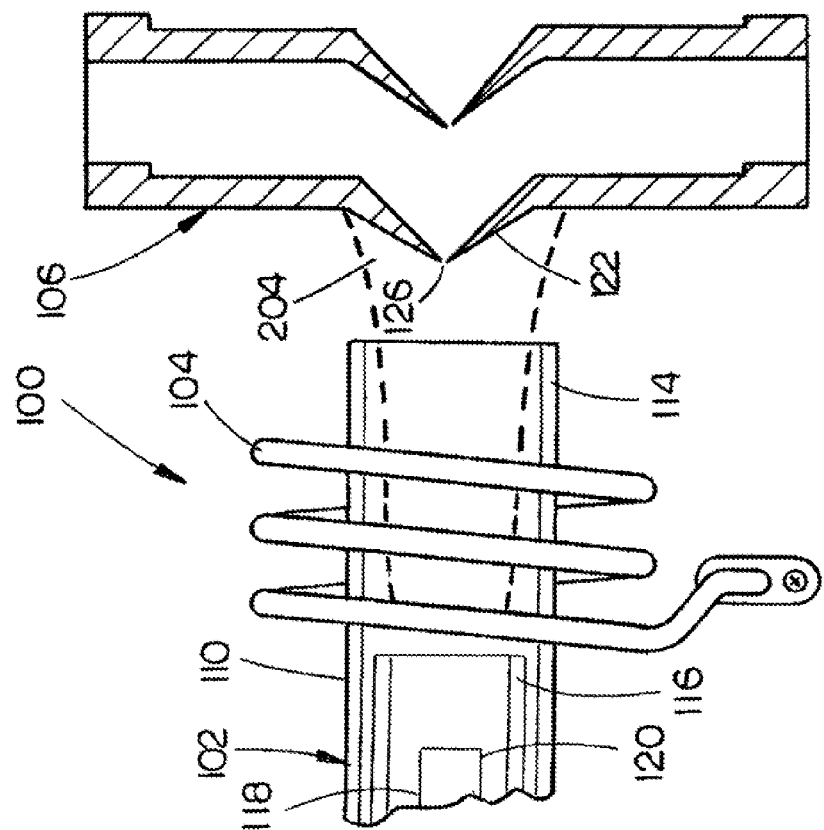

TORCH ASSEMBLY

CROSS-REFERENCE TO RELATED APPLICATIONS

The present applications claims the benefit under 35 U.S.C. §119(e) of U.S. Provisional Application Ser. No. 61/322,740, filed Apr. 9, 2010, and titled TORCH ASSEMBLY, which is herein incorporated by reference in its entirety.

BACKGROUND

Inductively coupled plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an inductively coupled plasma mass spectrometer (ICP/ICPMS), an inductively coupled plasma atomic emission spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICPMS or ICP-AES instruments for analysis.

SUMMARY

A plasma torch assembly suitable for use in ICP spectrometry is described. In an implementation, the plasma torch assembly comprises a first tube and a second tube supported by a torch body. The torch body includes a first bore configured to receive an end of the first tube, a second bore configured to receive an end of the second tube, and a manifold disposed between the first bore and the second bore to receive a flow of gas for injection between the first tube and the second tube. The manifold has an outer diameter at least substantially equal to the inner diameter of the first tube and an inner diameter at least substantially equal to the outer diameter.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. In the figures, the use of the same reference numbers in different instances in the description and the figures may indicate similar or identical items.

FIGS. 4A and 4B illustrate the effect of reducing the flow of gas supplied to the plasma torch on the plasma field.

DETAILED DESCRIPTION

Overview

Figure 1:
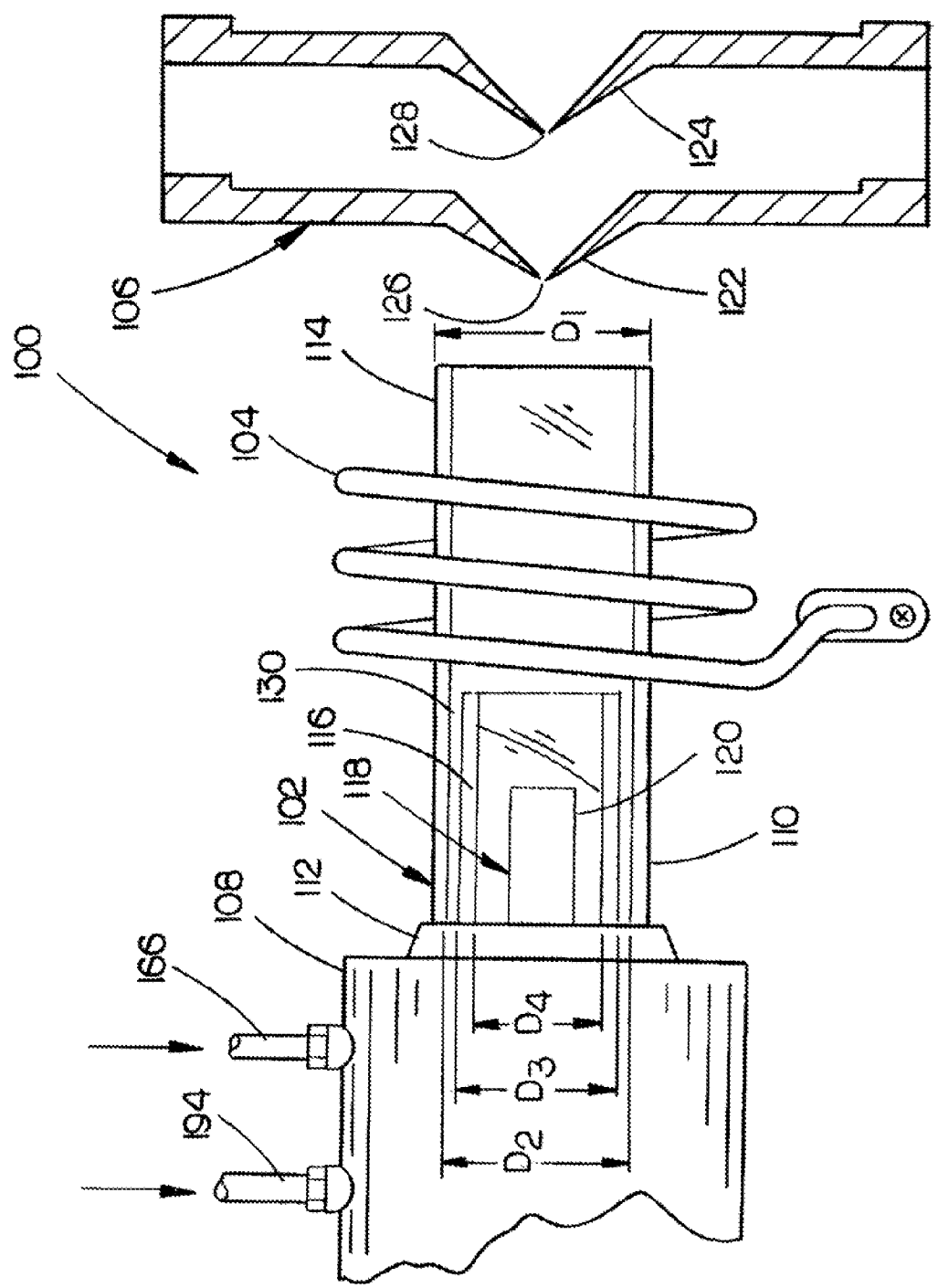
FIG. 1 is an illustration of an ICP spectrometry system in an example implementation that employs a plasma torch assembly.

Inductively coupled plasma (ICP) used for spectrometry is sustained in a plasma torch, such as a Fassel torch, or the like, that is formed of three concentric tubes. The end of the outer tube of the plasma torch is placed inside an induction coil supplied with a radio-frequency electric current. A plasma-forming gas is then introduced between the outermost tubes of the plasma torch. The induction coil causes the plasma-forming gas to become energized via electromagnetic induction to create a high temperature plasma region within the torch.

The temperature of the plasma within the plasma torch is very high, on the order of 10,000K. Consequently, to prevent damage to the plasma torch, the plasma is constrained within the torch via the flow of plasma-forming gas injected between the outermost tubes. The plasma-forming gas keeps the ICP discharge away from the outer tube of the plasma torch to protect the torch from the high temperature plasma. The gas also helps to stabilize the ICP discharge.

To adequately form the ICP discharge region, while providing adequate separation between the high temperature plasma and the outer tube, the flow of plasma-forming gas used by the plasma torch is usually very high. For example, in a conventional Fassel torch of standard size (e.g., having an outer tube with an inner diameter of between approximately 16 mm to approximately 22 mm), the flow rate of the plasma-forming gas, which is typically argon (Ar), must be approximately 12-14 L/min in order for the ICP spectrometry system to function adequately.

Accordingly, a plasma torch assembly is described that facilitates the use of lower flow rate plasma-forming gas (e.g., Argon (Ar)) while providing adequate separation of high temperature plasma from the components of the torch assembly and allowing satisfactory function of the ICP spectrometry system. In implementations, the plasma torch assembly comprises a demountable plasma torch that includes concentric first (outer) and second (intermediate) tubes supported by a torch body. The second tube is disposed concentrically within the first tube and thus has an outer diameter that is less than the inner diameter of the first tube. The torch body includes a first bore configured to receive an end of the first tube and a second bore configured to receive an end of the second tube. A manifold is disposed between the first bore and the second bore to receive a plasma-forming gas for injection between the first tube and the second tube. The manifold has an outer diameter at least substantially equal to the inner diameter of the first tube and an inner diameter at least substantially equal to the outer diameter of the second tube. In this manner, the flow pattern of the plasma-forming gas is improved.

The torch body further includes a cylinder configured to receive an injector assembly that supplies a carrier gas containing a nebulized sample. The injector assembly includes a base that is received in the channel that supports a third (inner) tube configured to be disposed concentrically within the second tube. The torch body includes a second manifold disposed between the second bore and the cylinder, and configured to receive an auxiliary gas to be injected between the second tube and the third tube. Like the first manifold, the second manifold has an outer diameter that is at least substantially equal to the inner diameter of the second tube and an inner diameter at least substantially equal to the outer diameter of the third tube. In this manner, the flow pattern of the auxiliary gas is improved.

Example ICP Spectrometry System

FIG. 1 illustrates components of an ICP spectrometry system 100 in an example implementation. As shown, the ICP spectrometry system 100 comprises a plasma torch assembly 102, a radio frequency (RF) induction coil 104 that is coupled to an RF generator (not shown), and an interface 106. The plasma torch assembly 102 includes a housing 108 that receives a plasma torch 110 configured to sustain the ICP. The plasma torch 110 includes a torch body 112, a first (outer) tube 114, a second (intermediate) tube 116, and an injector assembly 118 which includes a third (injector) tube 120.

The plasma torch 110 is mounted horizontally by the housing 108 and positioned centrally in the RF induction coil 104 so that the end of the first (outer) tube 114 is adjacent to (e.g., 10-20 mm from) the interface 106. The interface 106 generally comprises a sampler cone 122 positioned adjacent to the ICP and a skimmer cone 124 positioned adjacent to the sampler cone 122, opposite the ICP. A small diameter opening 126, 128 is formed in each cone 122, 124 at the apex of the cone 122, 124 to allow the passage of ions from the ICP for analysis.

A flow of gas (e.g., the plasma-forming gas), which is used to form the ICP, is passed between the first (outer) tube 114 and the second (intermediate) tube 116. A second flow of gas (e.g., the auxiliary gas) is passed between the second (intermediate) tube 116 and the third (injector) tube 120 of the injector assembly 118. The second flow of gas is used to change the position of the base of the ICP relative to the ends of the second (intermediate) tube 116 and the third (injector) tube 120. In typical implementations, the plasma-forming gas and the auxiliary gas comprise argon (Ar). However, it is contemplated that other gases may be used instead of or in addition to argon (Ar), in specific implementations.

The RF induction coil 104 surrounds the first (outer) tube 114 of the plasma torch 110. RF power (e.g., 750-1500 W) is applied to the coil 104 to generate an alternating current within the coil 104. Oscillation of this alternating current (typically 27 or 40 MHz) causes an electromagnetic field to be created in the plasma-forming gas within the first (outer) tube 114 of the plasma torch 110 to form an ICP discharge through inductive coupling.

A carrier gas is then introduced into the third (injector) tube 120 of the injector assembly 118. The carrier gas passes through the center of the plasma, where it forms a channel that is cooler than the surrounding plasma. Samples to be analyzed are introduced into the carrier gas for transport into the plasma region, usually as an aerosol of liquid formed by passing the liquid sample into a nebulizer. As a droplet of nebulized sample enters the central channel of the ICP, it evaporates and any solids that were dissolved in the liquid vaporize and then break down into atoms. In typical implementations, the carrier gas may comprise argon (Ar). However, it is contemplated that other gases may be used instead of, or in addition to, argon (Ar) in specific implementations.

Example Plasma Torch

FIGS. 2A, 2B, 3A, and 3B illustrate the plasma torch 110 shown in FIG. 1 in greater detail. The plasma torch 110 is illustrated as including concentric first (outer) and second (intermediate) tubes 114, 116. The first tube 114 is illustrated as having constant outer and inner diameters ($D_1$ and $D_2$, respectively). The second tube 116 is similarly illustrated as having constant outer and inner diameters ($D_3$ and $D_4$, respectively). As shown, the second tube 116 is disposed concentrically within the first tube 114 so that the outer diameter ($D_3$) of the second tube 116 is less than the inner diameter $D_2$ of the first tube 114. In this manner, an elongated toroid (e.g., ring-shaped) volume 130 is formed between the first tube 114 and the second tube 116 that has a constant width $W_{P1}$, where $W_{P1} = \frac{1}{2}(D_2 - D_3)$.

The concentric first and second tubes 114, 116 are supported by the torch body 112. The torch body 112 includes a first bore 132 configured to receive a proximate end 134 of the first tube 114 and a second bore 136 configured to receive a proximate end 138 of the second tube 116 so that the first and second tubes 114, 116 are supported in a cantilevered fashion. For example, as shown, each bore 132, 136 is cylindrical in shape and is sized to receive the proximate ends 134, 138 of the respective first and second tubes 114, 116. Each bore 132, 136 includes an outer wall 140, 142 (with a diameter $D_5$ and $D_6$, respectively) and an end wall 144, 146, respectively, against which the proximate ends 134, 138 abut when the first and second tubes 114, 116 are received in the torch body. In embodiments, the diameters ($D_5$ and $D_6$, respectively) of the outer walls 140, 142 may be slightly smaller than the corresponding diameters $D_1$ and $D_3$ of the respective first and second tubes 114, 116 (e.g., $D_5 < D_1$ and $D_6 < D_3$) when the first and second tubes 114, 116 are not received within the bores 132, 136 to provide an interference fit between the tubes 114, 116 and the torch body 112. In this manner, the tubes 114, 116 may be secured within the torch body 112 without additional mounting hardware such as seals, O-rings, or the like.

Figure 3A:
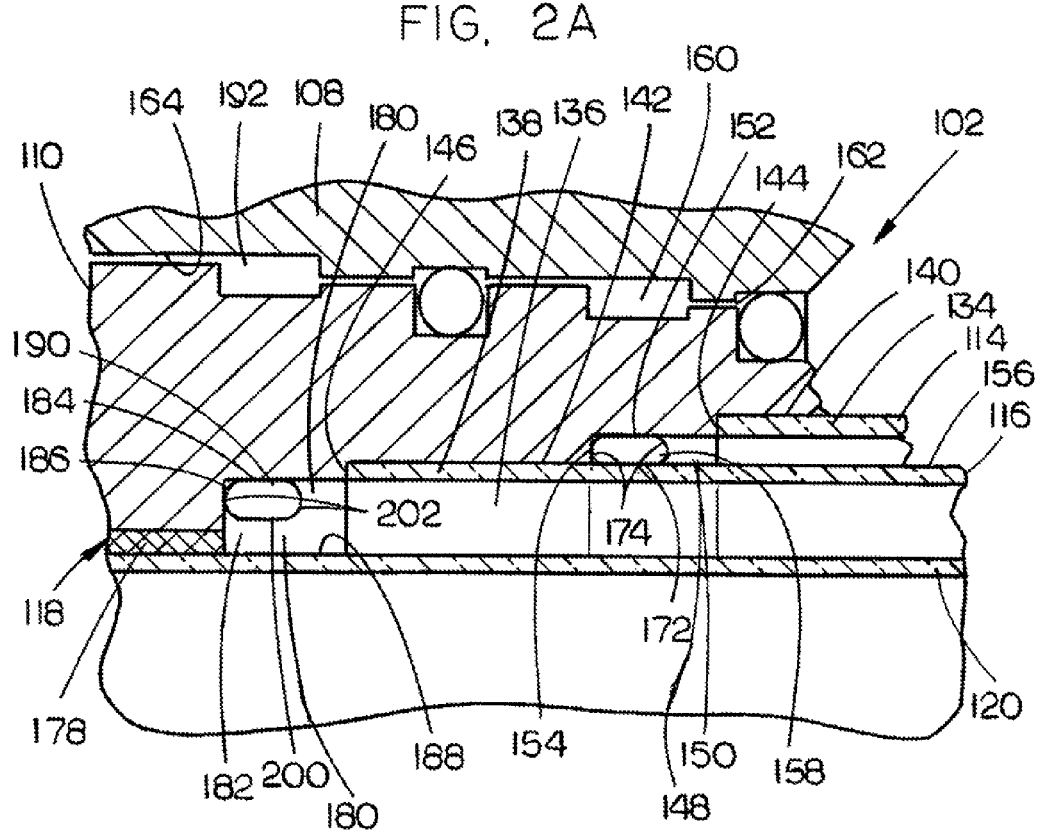
FIGS. 3A and 3B are partial cross-sectional views of the plasma torch shown in FIGS. 2A and 2B, further illustrating the first manifold and second manifold.
Figure 3B:
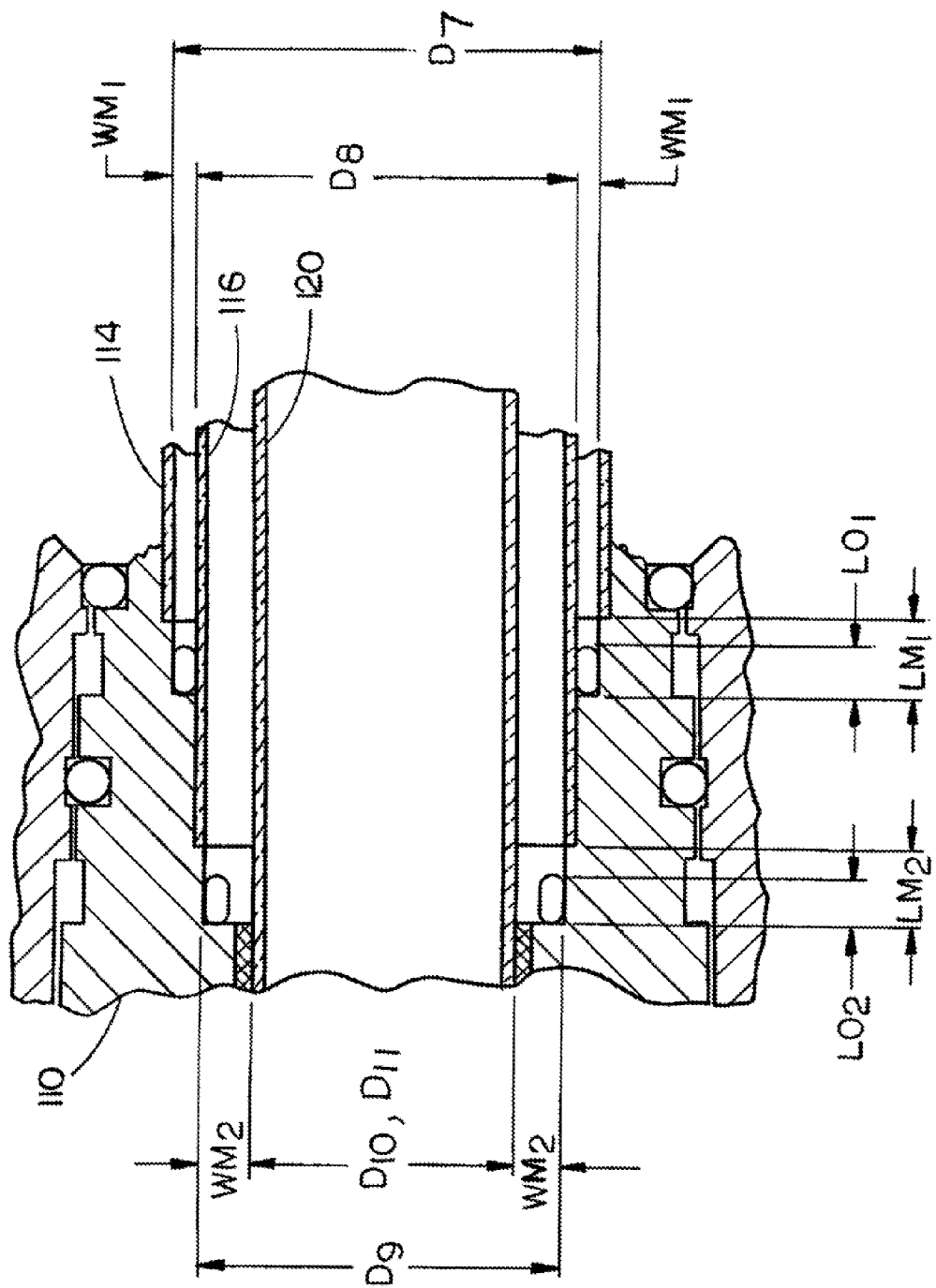

The torch body 112 includes a manifold 148 to receive a flow of plasma-forming gas for injection into the plasma torch 110 between the first tube 114 and the second tube 116. As shown in FIGS. 3A and 3B, the manifold 148 is positioned along the length of the torch body 112 between the first bore 132 and the second bore 136. The manifold 148 comprises a toroid volume 150 having an at least substantially rectangular cross-section defined by an outer wall 152 and an end wall 154 formed in the torch body 112. The outer wall 152, and thus the manifold 148 itself, has an outer diameter ($D_7$) that is at least substantially equal to, and in implementations is equal to, the inner diameter ($D_2$) of the first tube 114 when the first tube 114 is received in the first bore 132. In the embodiment illustrated, the inner wall of the manifold 148 is provided by the outer surface 156 of the second tube 116. Consequently, the inner diameter ($D_8$) of the manifold 148 is at least substantially equal to, and in implementations is equal to, the outer diameter ($D_3$) of the second tube 116 when the second tube is received in the second bore 136. The width of the manifold ($W_{M1}$), where $W_{M1} = \frac{1}{2}(D_7 - D_8)$, is thus at least substantially equal to, and in implementations may be equal to, the width of the elongated toroid volume 130 between the first tube 114 and the second tube 116 ($W_{P1}$). The manifold 148 has a length ($L_{M1}$). Thus, the manifold 148 has a cross-sectional area ($A_{M1}$ where $A_{M1} = L_{M1} \times W_{M1}$).

In implementations, the length of the manifold 148 ($L_{M1}$) is greater than the width of the manifold ($W_{M1}$), e.g., the manifold 148 is longer than the width ($W_{P1}$) of the space between the first tube 114 and the second tube 116. In implementations, the walls of the manifold 148 are formed so that the surfaces of the manifold (surfaces 152, 154, and 156) are at least substantially smooth with no obstructions to block the flow of gas within the manifold 148.

One or more orifices 158 are formed in the outer wall 152 of the manifold 148 to receive the flow of plasma-forming gas into the manifold 148 to be injected into the elongated toroid volume 130 between the first and second tubes 114, 116. In the implementation illustrated, the orifices 158 couple the manifold 148 to an annulus 160 formed by the outer surface 162 of the torch body 112 and the inner surface 164 of the housing 108. The orifices 158 port a flow of plasma-forming gas supplied to the annulus 160 through the housing 108 via line 166 (see FIG. 1) into the manifold 148.

Figure 2A:
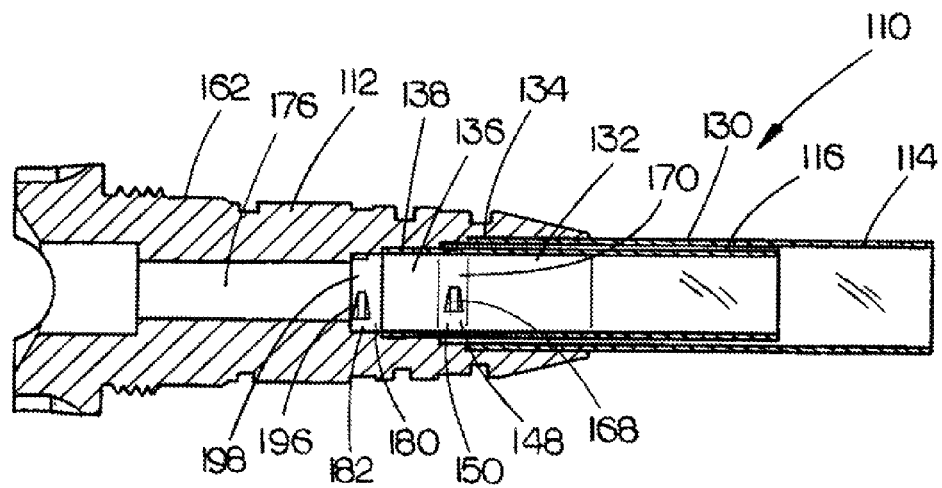
FIGS. 2A and 2B are cross-sectional views illustrating the plasma torch shown in FIG. 1.
Figure 2B:
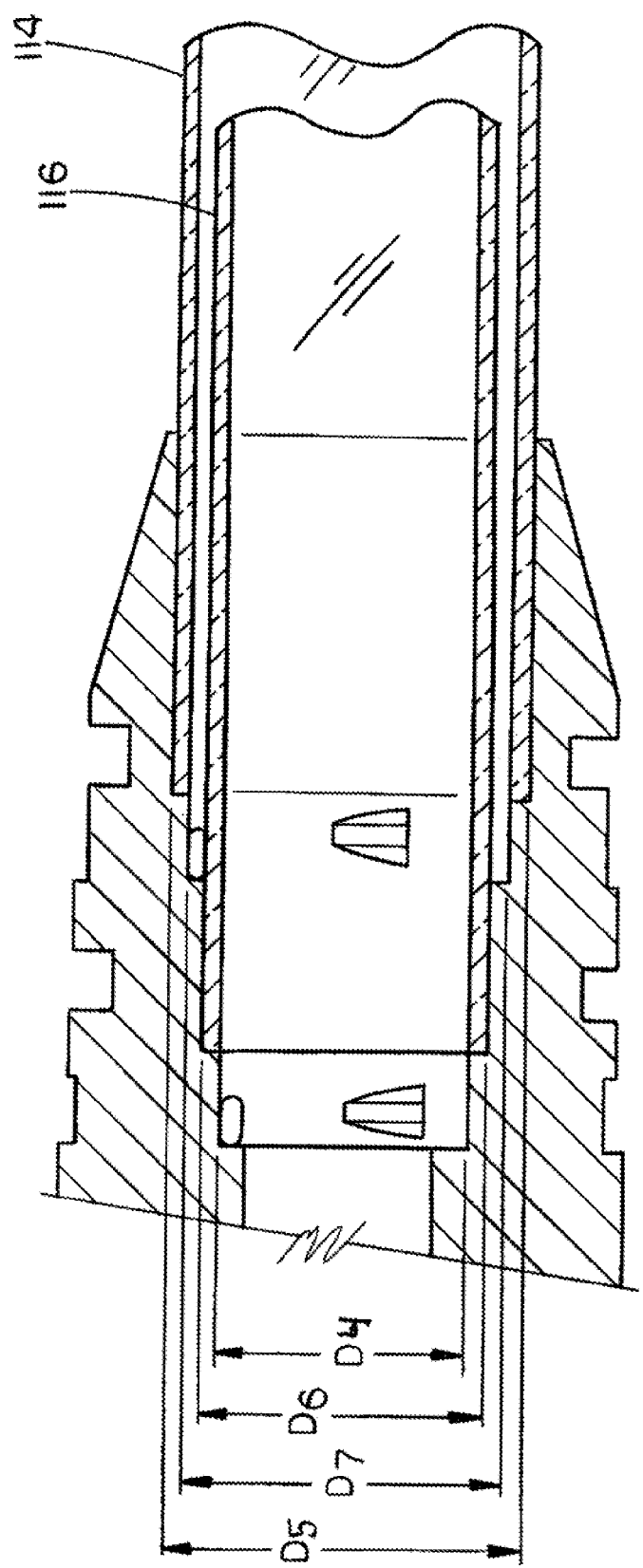

As shown, the orifices 158 intersect the surface of the outer wall 152 tangentially, forming a generally scoop-shaped depression 168 in the surface 170 of the wall 152 due to the curvature of the wall 152. Thus, the orifices 158 may be viewed as being elongated in shape when viewed in cross-section. The orifices 158 have a cross-sectional area ($A_{O1}$). As shown in FIGS. 2A and 2B, the orifices 158 may be generally circular in cross section. However, orifices 158 having other cross-sectional shapes are contemplated. For example, as shown in FIGS. 3A and 3B, orifices 158 having generally straightened horizontal edges 172 and curved (e.g., rounded) vertical edges 174, and thus an elongated cross-section, are possible. The orifices 158 shown in FIGS. 3A and 3B are further illustrated as being positioned adjacent to end wall 154 and having a length ($L_{O1}$) that is at least equal to or greater than half of the length of the manifold 148 ($L_{M1}$). Orifices 158 having other cross sectional shapes (e.g., elliptical) are possible.

In one or more implementations, the cross-sectional areas ($A_{O1}$) of the orifices 158 are at least approximately equal to the cross-sectional area ($A_{M1}$) of the manifold 148. In specific implementations, the cross-sectional areas ($A_{O1}$, $A_{M1}$) of the manifold and orifice 158 may range from between about 4.2 square millimeters (4.2 mm$^2$) to about 6.2 square millimeters (6.2 mm$^2$). For instance, in one example, the manifold 148 may be fabricated to have a length of 5 millimeters ($L_{M1}$=5 mm) and a width of 1 millimeter ($W_{M1}$=1 mm) so that the cross-sectional area of the manifold is 5 square millimeters ($A_{M1}$=5 mm$^2$). In this example, each orifice 158, which is circular, may be fabricated to have a diameter of about 2.5 millimeters to about 2.8 millimeters so that the cross-sectional area of the orifice is also approximately 5 square millimeters ($A_{O1}$=5 mm$^2$) to about 6.2 square millimeters ($A_{O1}$=6.2 mm$^2$). In another example, wherein the manifold 148 has similar dimensions (e.g., a length of five millimeters ($L_{M1}$=5 mm), a width of 1 millimeter ($W_{M1}$=1 mm), and a cross-sectional area of 5 square millimeters ($A_{M1}$=5 mm$^2$)), each orifice 158, which may be elongated, and may be fabricated to have a cross sectional area of 4.2 square millimeters ($A_{O1}$=4.2 mm$^2$). Other examples are possible.

The torch body 112 further includes an injector assembly receiving cylinder 176 configured to receive the injector assembly 118, which supplies the carrier gas containing a nebulized sample. The injector assembly 118 includes a base 178 that is received in the cylinder 176. The base 178 supports the third (inner) tube 120 so that the third tube 120 is disposed concentrically within the second tube 116 when the injector assembly 118 is received in the plasma torch 110.

A second manifold 180 is provided in the torch body 112 to receive a flow of auxiliary gas for injection into the plasma torch 110 between the second tube 116 and the third tube 120. The second manifold 180 is positioned along the length of the torch body 112 between the second bore 136 and the injector assembly 118 receiving cylinder 176. As shown, the second manifold 180, like the first manifold 148, comprises a toroid volume 182 having an at least substantially rectangular cross-section defined by an outer wall 184 formed in the torch body 112 and an end wall 186 formed by the torch body 112 and injector assembly base 178. The outer wall 184, and thus the second manifold 180 itself, has an outer diameter ($D_9$) that is at least substantially equal to, and in implementations may be equal to, the inner diameter ($D_4$) of the second tube 116 when the second tube 116 is received in the second bore 136. In the embodiment illustrated, the inner wall of the second manifold 180 is provided by the outer surface 188 of the third tube 120. Thus, the inner diameter ($D_{10}$) of the second manifold 180 is at least substantially equal to, and in implementations may be equal to, the outer diameter ($D_{11}$) of the third tube 120 when the injector assembly 118 is received in the plasma torch 110. The width of the second manifold 180 ($W_{M2}$), where $W_{M2}=\frac{1}{2}(D_9-D_{10})$, is thus at least substantially equal to, and in implementations may be equal to, the width of the elongated toroid volume between the second tube 116 and the third tube 120 ($W_{P2}$). The second manifold 180 has a length ($L_{M2}$). Thus, the second manifold 180 has a cross-sectional area ($A_{M2}$, where $A_{M2}=L_{M2} \times W_{M2}$). In implementations, the length of the second manifold 180 ($L_{M2}$) is greater than the width of the second manifold ($W_{M2}$), e.g., the second manifold 180 is longer than the width ($W_{P2}$) of the space between the second tube 116 and the third tube 120. In implementations, the walls of the manifold 180 are formed so that the surfaces of the second manifold 180 (surfaces 184, 186, 188) are at least substantially smooth with no obstructions to block the flow of gas within the second manifold 180.

One or more orifices 190 are formed in the outer wall 184 of the second manifold 180 to receive the flow of auxiliary gas into the manifold 180 to be injected into the toroid volume between the second and third tubes 116, 120. As shown, each orifice 190 is coupled to an annulus 192 formed by the outer surface 162 of the torch body 112 and the inner surface 164 of the housing 108 to port a flow of auxiliary gas supplied to the housing 108 via line 194 (see FIG. 1) into the manifold 180.

As shown, the orifices 190 intersect the surface 198 of the outer wall 184 tangentially, forming a generally scoop-shaped depression 196 in the surface 198 of the wall 184 due to the curvature of the wall 184. As shown in FIGS. 2A and 2B, the orifices 190 may be generally circular in cross section. However, orifices 190 having other cross-sectional shapes are contemplated. For example, as shown in FIGS. 3A and 3B, orifices 190 having generally straightened horizontal edges 200 and curved (e.g., rounded) vertical edges 202, and thus an elongated cross-section, are possible. The orifices 190 shown in FIGS. 3A and 3B are further illustrated as being positioned adjacent to end wall 186 and having a length ($L_{O1}$) that is at least equal to or greater than half of the length of the manifold 148 ($L_{M1}$). Orifices 190 having other cross sectional shapes (e.g., elliptical) are possible.

In implementations, the first, second, and third tubes 114, 116, 120 may be fabricated of quartz, while the torch body 112 and the base 178 of the injector assembly 118 are formed of polytetrafluoroethylene (PTFE). However, it is contemplated that the first, second, and third tubes 114, 116, 120 may be made from materials other than quartz, such as alumina, platinum, and sapphire, for example, when highly corrosive materials are to be analyzed.

The plasma-forming gas (e.g., argon (Ar)) is introduced into the manifold 148 tangentially through the one or more orifices 158, which causes the gas to swirl tangentially around the outer surface 156 of the second tube 116 within the manifold 148. The swirling gas stream is maintained by the second tube 116 until the plasma-forming gas reaches the first turn of the RF induction coil 104. By introducing the plasma-forming gas tangentially through the one or more orifices 158, turbulence is minimized within the toroid volume 150 of the manifold 148, which may have an at least substantially rectangular cross-section, so that the flow is at least substantially laminar. Further, because the width of the manifold 148 ($W_{M1}$) is at least substantially equal to, and in implementations may be equal to, the width of the elongated toroid volume 130 between the first tube 114 and the second tube 116 ($W_P$), there are no protrusions to create turbulence within the flow. Thus, the flow of the plasma-forming gas between the first tube 114 and the second tube 116 remains at least substantially laminar.

In this manner, the flow pattern of the plasma-forming gas is improved, allowing the flow rate of the plasma-forming gas to be reduced in comparison with the flow rate required by a conventional Fassel torch of the same or similar size. Moreover, the flow rate may be reduced while maintaining adequate separation of the high temperature plasma from the first tube 114 of the plasma torch 110 and providing satisfactory function of the ICP spectrometry system 100.

Similarly, the auxiliary gas (e.g., argon (Ar)) is introduced into the second manifold 180 tangentially through the one or more orifices 190, which causes the gas to swirl tangentially around the outer surface 188 of the third tube 120 within the second manifold 180. The swirling gas stream is maintained by the third tube 120 until the auxiliary gas reaches the end of the third tube 120. By introducing the auxiliary gas tangentially through the one or more orifices 190, turbulence is minimized within the toroid volume 182 of the second manifold 180 so that the flow is at least substantially laminar. Further, because the width of the second manifold ($W_{M2}$) is at least substantially equal to, and in implementations may be equal to, the width of the elongated toroid volume 130 between the first tube 114 and the second tube 116 ($W_{P2}$), there are no protrusions to create turbulence within the flow. Thus, the flow of the auxiliary gas between the second tube 116 and the third tube 120 remains at least substantially laminar.

In this manner, the flow pattern of the plasma-forming and auxiliary gases are improved, allowing the flow rates of the plasma-forming and/or the auxiliary gas, which are typically both argon (Ar), to be reduced in comparison with the flow rate required by a conventional Fassel torch of the same or similar size. Moreover, the flow rate may be reduced while maintaining adequate separation of the high temperature plasma from the first tube 114 of the plasma torch 110 and providing satisfactory function of the ICP spectrometry system 100.

In implementations where the inner diameter of the first tube 112 is between approximately 16 mm to approximately 22 mm (e.g., similar in size to a conventional Fassel torch), the combined flow rate of plasma-forming gas (e.g., Argon (Ar)) and auxiliary gas (e.g., Argon (Ar) may be reduced, so that the plasma-forming gas and auxiliary gas are injected at a combined rate of less than about 10 L/min, while maintaining adequate separation of the high temperature plasma from the first tube 114 of the plasma torch 110 and providing satisfactory function of the ICP spectrometry system 100. In some implementations where the inner diameter of the first tube 112 is between approximately 16 mm to approximately 22 mm, the plasma-forming gas and the auxiliary gas may be injected at a combined flow rate of about 4 L/min to about 10 L/min, while maintaining adequate separation of the high temperature plasma from the first tube 114 and providing satisfactory function of the ICP spectrometry system 100. In such instances, the plasma-forming gas may have a flow rate of between about 4 L/min and about 9 L/min. The flow rate of the auxiliary gas is typically lower than the flow rate of the plasma-forming gas, on the order of about 0 L/min to about 1 L/min, and in some instances from about 0.5 L/min to about 1 L/min.

FIGS. 4A and 4B illustrate the effect of reducing the flow of the plasma-forming gas, in this case argon (Ar), on the plasma field 204 formed in the ICP spectrometry system 100 of FIG. 1. More specifically, FIG. 4A illustrates the plasma field 204 generated by the plasma torch 110 when the flow rate of argon is 12 L/min. Flow rates of this order (e.g., greater than about 12 L/min) are generally necessary to adequately sustain the plasma field, and thus provide adequate performance of ICP spectrometry systems that employ conventional Fassel torches of the same or similar size.

FIG. 4B illustrates the plasma field 204 generated by the plasma torch 110 when the flow rate of plasma-forming gas is reduced to 9 L/min. The plasma field 204 generated at this flow rate is approximately eighty percent (80%) of plasma field 204 generated when a flow rate of 12 L/min is utilized, as shown in FIG. 4A, and is sufficient to maintain adequate performance of the ICP spectrometry system 100. Moreover, it is contemplated that lower flow rates may continue to yield plasma fields 204 that allow for adequate performance of the ICP spectrometry system 100. For example, in one implementation, a flow rate of about 5 L/min has been found to allow adequate performance of the ICP spectrometry system 100. Thus, it is contemplated that the plasma torch 110 described may yield reductions in the amount of plasma-forming gas (e.g., argon (Ar)) used on the order of about fifty percent (50%), although greater or lesser reductions are contemplated depending on specific implementation requirements.

In various implementations, the size of the plasma torch assembly 102 may be increased or decreased. Thus, the flow rates of plasma-forming gas utilized by such torches may thus be greater or less than the flow rates of plasma-forming gas used by the plasma torch shown in FIGS. 4A and 4B. Nevertheless, it is contemplated that similar reduction in the amount of plasma-forming gas used by such larger or smaller plasma torches 110 (e.g., on the order of fifty percent (50%)) may be furnished.

CONCLUSION

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:
1. A plasma torch comprising:
a first tube having an inner diameter;
a second tube disposed concentrically within the first tube, the second tube having an outer diameter that is less than the inner diameter of the first tube, the outer diameter of the second tube having a substantially constant spacing from the inner diameter of the first tube; and a body including a first bore configured to receive an end of the first tube, a second bore configured to receive an end of the second tube, and a manifold disposed between the first bore and the second bore and configured to receive a flow of gas for injection between the first tube and the second tube, the manifold having an outer diameter at least substantially equal to the inner diameter of the first tube and an inner diameter at least substantially equal to the outer diameter of the second tube when the second tube is received in the second bore, the manifold having a width that is substantially equal to the substantially constant spacing between the outer diameter of the second tube and the inner diameter of the first tube.

2. The plasma torch as recited in claim 1, wherein the manifold comprises a toroid volume having an at least substantially rectangular cross-section, the rectangular cross section having a length and a width, wherein the length is greater than the width.

3. The plasma torch as recited in claim 1, wherein the manifold comprises a ring-shaped exterior wall, and wherein an outer wall of the second tube forms an interior wall of the manifold.

4. The plasma torch as recited in claim 3, wherein the manifold comprises an orifice formed in the exterior wall and configured to receive the flow of gas, the manifold having a first cross-sectional area and the orifice having a second cross-sectional area, wherein the first cross-sectional area and the second cross-sectional area are at least approximately equal.

5. The plasma torch as recited in claim 1, wherein the body further comprises a cylinder configured to receive an injector assembly, the injector assembly including a base configured to be received in the channel and a third tube configured to be disposed concentrically within the second tube to supply a carrier gas containing a nebulized sample, the third tube having an outer diameter that is less than an inner diameter of the second tube.

6. The plasma torch as recited in claim 5, wherein the body further includes a second manifold disposed between the second bore and the cylinder and configured to receive a second flow of gas to be injected between the second tube and the third tube, the second manifold having an outer diameter at least substantially equal to the inner diameter of the second tube and an inner diameter at least substantially equal to the outer diameter of the third tube.

7. The plasma torch as recited in claim 5, wherein the second manifold comprises a generally ring-shaped exterior wall, and wherein an outer wall of the third tube forms an interior wall of the second manifold.

8. The plasma torch as recited in claim 7, wherein the second manifold comprises an orifice formed in the exterior wall and configured to receive the second flow of gas injected into the second manifold.

9. The plasma torch as recited in claim 6, wherein the inner diameter of the first tube is between approximately 16 mm to approximately 22 mm, and the flow of gas and the second flow of gas are injected at a combined flow rate of less than about 10 L/min.

10. The plasma torch as recited in claim 9, wherein the flow of gas and the second flow of gas are injected at a combined flow rate of about 4 L/min to about 10 L/min.

11. The plasma torch as recited in claim 1, wherein the manifold causes the flow of gas injected between first tube and the second tube to be at least substantially laminar.

12. A torch body for a plasma torch comprising:
a singular body portion defining each of:
a first bore configured to receive an end of a first tube, the first tube having an inner diameter and an outer diameter, the first bore having an outer wall diameter that is substantially equal to the outer diameter of the first tube,
a second bore configured to receive an end of a second tube so that the second tube is held within the first tube and the first tube and the second tube are concentric, the second tube having an outer diameter; and
a manifold disposed between the first bore and the second bore and configured to receive a flow of gas to be injected between the inner tube and the outer tube, the manifold having an outer diameter equal to the inner diameter of the first tube when the first tube is received in the first bore and an inner diameter equal to the outer diameter of the second tube when the second tube is received in the second bore.

13. The torch body as recited in claim 12, wherein the manifold comprises a toroid volume having an at least substantially rectangular cross-section and a first cross-sectional area, the manifold having an exterior wall and an orifice formed in the exterior wall and configured to receive the flow of gas injected into the manifold, the orifice having a second cross-sectional area, wherein the first cross-sectional area and the second cross-sectional area are at least approximately equal.

14. The torch body as recited in claim 12, wherein the body further comprises a cylinder configured to receive an injector assembly, the injector assembly including a base configured to be received in the channel and a third tube configured to be disposed concentrically within the second tube to supply a carrier gas containing a nebulized sample, the third tube having an outer diameter that is less than an inner diameter of the second tube.

15. The torch body as recited in claim 14, wherein the body further includes a second manifold disposed between the second bore and the cylinder and configured to receive a second flow of gas to be injected between the second tube and the third tube, the second manifold having an outer diameter equal to the inner diameter of the second tube when the second tube is received in the second bore and an inner diameter equal to the outer diameter of the third tube when the injector assembly is received in the cylinder.

16. The torch body as recited in claim 15, wherein the second manifold comprises a toroid volume having an at least substantially rectangular cross-section and an exterior wall, and wherein the second manifold comprises an orifice formed in the exterior wall and configured to receive the flow of gas injected into the second manifold.

17. The torch body as recited in claim 15, wherein the inner diameter of the first tube is between approximately 16 mm to approximately 22 mm, and the flow of gas and the second flow of gas are injected at a combined flow rate of less than about 10 L/min.

18. The torch body as recited in claim 12, wherein the manifold causes the flow of gas injected between the first tube and the second tube to be at least substantially laminar.

* * * * *